US010868992B2

United States Patent
Nakamura

(10) Patent No.: US 10,868,992 B2
(45) Date of Patent: Dec. 15, 2020

(54) ENDOSCOPE APPARATUS AND ENDOSCOPE

(71) Applicant: OLYMPUS CORPORATION, Tokyo (JP)

(72) Inventor: Sho Nakamura, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 48 days.

(21) Appl. No.: 16/192,944

(22) Filed: Nov. 16, 2018

(65) Prior Publication Data

US 2019/0089920 A1    Mar. 21, 2019

Related U.S. Application Data

(63) Continuation of application No. PCT/JP2016/065923, filed on May 30, 2016.

(51) Int. Cl.
*H04N 5/3745*    (2011.01)
*H04N 5/225*    (2006.01)
(Continued)

(52) U.S. Cl.
CPC ..... *H04N 5/37457* (2013.01); *A61B 1/00006* (2013.01); *A61B 1/00029* (2013.01);
(Continued)

(58) Field of Classification Search
CPC ............ A61B 1/00006; A61B 1/00029; A61B 1/00114; A61B 1/00124; A61B 1/04;
(Continued)

(56) References Cited

U.S. PATENT DOCUMENTS 4,792,932 A * 12/1988 Bowhers ............ G01R 31/2834
324/76.44
5,396,579 A * 3/1995 Koji .................... G06G 7/26
706/5

(Continued)

FOREIGN PATENT DOCUMENTS

CN    104640494 A    5/2015
JP    2002074663 A  * 3/2002
(Continued)

OTHER PUBLICATIONS

International Search Report dated Aug. 16, 2016 issued in PCT/JP2016/065923.
(Continued)

*Primary Examiner* — Joon Kwon
(74) *Attorney, Agent, or Firm* — Scully, Scott, Murphy & Presser, P.C.

(57) ABSTRACT

An endoscope apparatus includes an endoscope including a cable and a sensor and a processor. The endoscope includes a differential amplifying section configured to differentially amplify an output signal from the sensor. The processor includes a power supply circuit configured to generate a reference voltage supplied to the differential amplifying section. The reference voltage generated by the power supply circuit of the processor is supplied to the differential amplifying section of the endoscope via the cable. An output signal of the differential amplifying section is detected by the processor via the cable.

13 Claims, 6 Drawing Sheets

(51) Int. Cl.
*A61B 1/00* (2006.01)
*A61B 1/05* (2006.01)
*H04N 5/369* (2011.01)
*G01K 7/24* (2006.01)
*G01R 27/26* (2006.01)
*A61B 1/04* (2006.01)
*G02B 7/04* (2006.01)

(52) U.S. Cl.
CPC ...... *A61B 1/00114* (2013.01); *A61B 1/00124* (2013.01); *A61B 1/04* (2013.01); *A61B 1/051* (2013.01); *G01K 7/24* (2013.01); *G01R 27/2611* (2013.01); *H04N 5/225* (2013.01); *H04N 5/3698* (2013.01); *G02B 7/04* (2013.01); *H04N 2005/2255* (2013.01)

(58) Field of Classification Search
CPC ...... A61B 1/051; G01K 7/24; G01R 27/2611; G02B 7/04; H04N 2005/2255; H04N 5/225; H04N 5/3698; H04N 5/37457
See application file for complete search history.

(56) References Cited

U.S. PATENT DOCUMENTS 6,059,720 A * 5/2000 Furusawa .......... A61B 1/00186
348/76
2009/0090763 A1 * 4/2009 Zemlok .................. A61B 90/98
227/175.2
2009/0123135 A1 * 5/2009 Amling .................. H04N 5/232
386/248
2013/0265403 A1 * 10/2013 Okawa .................. A61B 1/045
348/76
2015/0190042 A1 7/2015 Segawa

FOREIGN PATENT DOCUMENTS

| | | |
|---|---|---|
| JP | 2007-202951 A | 8/2007 |
| JP | 2009-195601 A | 9/2009 |
| JP | 2015-142696 A | 8/2015 |
| JP | 2015-192695 A | 11/2015 |

OTHER PUBLICATIONS

Jianhua, Zou. et al., "Differential Input Operation Circuit", published by Huazhong University of Science and Technology, pp. 232-236 (Jan. 31, 2015), with English translation of relevant part cited in the Office Action.

* cited by examiner

ENDOSCOPE APPARATUS AND ENDOSCOPE

CROSS REFERENCE TO RELATED APPLICATION

This application is a continuation application of PCT/JP2016/065923 filed on May 30, 2016, the entire contents of which are incorporated herein by this reference.

BACKGROUND OF INVENTION

1. Field of the Invention

The present invention relates to an endoscope apparatus and an endoscope.

2. Description of the Related Art

Conventionally, an endoscope apparatus including an endoscope that picks up an image of an object inside a subject, a processor that generates an observation image of the object, the image of which is picked up by the endoscope, and a monitor that displays the observation image generated by the processor has been widely used in a medical field, an industrial field, and the like.

In the endoscope, various sensors such as an image pickup device such as a CCD image sensor or a CMOS image sensor and a magnetic coil for endoscope shape detection are disposed. Input and output signals of the various sensors are transmitted to, via a long cable, a connector section (i.e., a connecting section to the processor) of the endoscope or a signal detection circuit disposed in the processor.

Because the input and output signals are transmitted via the long cable, a power supply voltage supplied from the processor to the sensors included in the endoscope and a voltage of a measurement signal outputted from the image pickup device of the endoscope to the processor are dropped by cable resistance. Therefore, means for correcting or reducing the voltage drop and fluctuation is necessary in order to stably and highly accurately detect measurement signals outputted from the sensors in the processor. For example, Japanese Patent Application Laid-Open Publication No. 2015-192695 proposes an endoscope apparatus that performs a countermeasure for a voltage drop by cable resistance.

In order to stabilize an output signal of an image pickup device disposed at an endoscope distal end, the endoscope apparatus of Japanese Patent Application Laid-Open Publication No. 2015-192695 determines a voltage value of a power supply for the image pickup device provided in a processor by measuring a voltage actually applied to the image pickup device.

SUMMARY OF THE INVENTION

An endoscope apparatus according to an aspect of the present invention is an endoscope apparatus including: an endoscope including a cable and a sensor; and a processor. The endoscope includes a differential amplifying section configured to differentially amplify an output signal from the sensor. The processor includes a reference-voltage generating section configured to generate a reference voltage supplied to the differential amplifying section. The reference voltage generated by the reference-voltage generating section of the processor is supplied to the differential amplifying section of the endoscope via the cable. An output signal of the differential amplifying section is detected by the processor via the cable.

An endoscope according to an aspect of the present invention is an endoscope including: a cable; a sensor; and a connector section. The endoscope includes a differential amplifying section configured to differentially amplify an output signal from the sensor. The connector section includes a reference-voltage generating section configured to generate a reference voltage supplied to the differential amplifying section. The reference voltage generated by the reference-voltage generating section of the connector section is supplied to the differential amplifying section via the cable. An output signal of the differential amplifying section is detected by the connector section via the cable.

DETAILED DESCRIPTION OF THE PREFERRED EMBODIMENT(S)

Embodiments of the present invention are explained below with reference to the drawings.

First Embodiment

Figure 1:
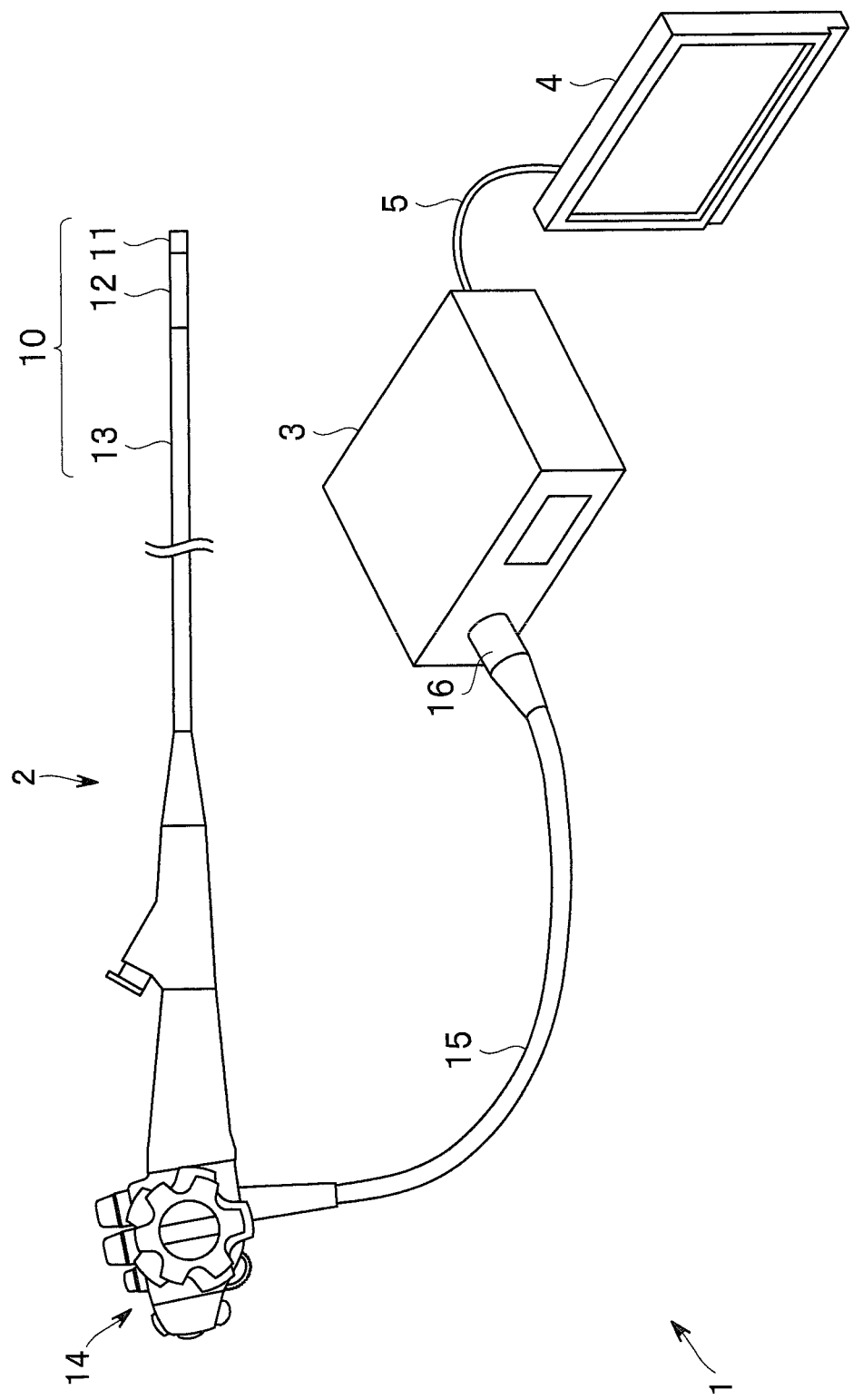
FIG. 1 is a configuration diagram showing a configuration of an endoscope apparatus according to a first embodiment.

FIG. 1 is a configuration diagram showing a configuration of an endoscope apparatus according to a first embodiment. As shown in FIG. 1, an endoscope apparatus 1 of this embodiment mainly includes an endoscope 2, a processor 3, and a monitor 4. The processor 3 and the monitor 4 are electrically connected via a cable 5.

The endoscope 2 of this embodiment can be introduced into a subject such as a human body and has a configuration for optically picking up an image of a predetermined observation part in the subject. Note that the subject into which the endoscope 2 is introduced is not limited to the human body but may be other organisms or may be artificial objects such as a machine and a building.

The endoscope 2 is configured mainly by an insertion section 10 inserted into the subject, an operation section 14 located at a proximal end of the insertion section 10, and a universal cable (hereinafter simply referred to as cable) 15 extending from a side portion of the operation section 14.

The insertion section 10 is configured by consecutively connecting a distal end portion 11 disposed at a distal end of the insertion section 10, a bendable bending section 12 disposed on a proximal end side of the distal end portion 11, and a flexible tube section 13 having flexibility disposed on a proximal end side of the bending section 12 and connected to a distal end side of the operation section 14.

The operation section 14 includes an up-down bending operation knob for bending the bending section 12 in an up-down direction, a left-right bending operation knob for bending the bending section 12 in a left-right direction, an air feeding/water feeding button for performing air feeding and water feeding, a suction button for performing suction, and switches for executing various endoscope functions.

A connector section 16 connected to the processor 3 is provided at a proximal end portion of the cable 15. The endoscope 2 is configured to be detachably connected to the processor 3 via the connector section 16.

The processor 3 performs driving and control of a lens of an image pickup unit explained below provided at the distal end portion 11. The processor 3 applies predetermined video signal processing to an image pickup signal outputted from an image pickup device of the image pickup unit explained below provided at the distal end portion 11, generates a predetermined video signal, and outputs the predetermined video signal to the monitor 4. That is, the processor 3 causes the monitor 4 to display, as a video, an optical image (an endoscopic image) picked up by the image pickup device.

A light source apparatus is formed integrally with the processor 3. That is, the processor 3 emits illumination light, which is emitted by a light source such as a halogen lamp or an LED, from a distal end face of the distal end portion 11 of the endoscope 2 toward an object via a light guide or the like inserted through the endoscope 2 and the processor 3.

Figure 2:
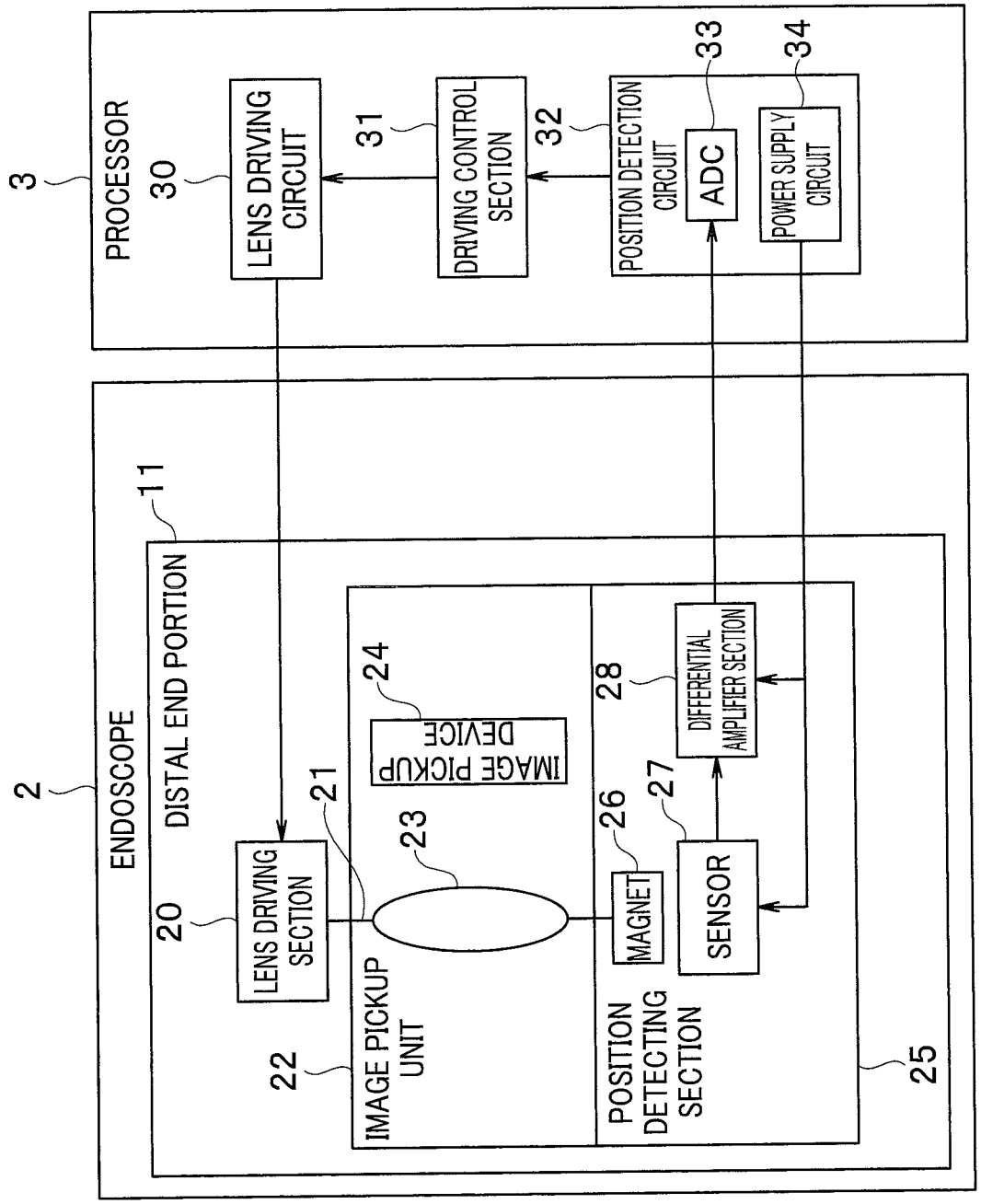
FIG. 2 is a configuration diagram for explaining detailed configurations of an endoscope and a processor.

FIG. 2 is a configuration diagram for explaining detailed configurations of the endoscope and the processor.

The distal end portion 11 of the endoscope 2 includes a lens driving section 20, a lens frame 21, an image pickup unit 22, and a position detecting section 25. The image pickup unit 22 includes an objective lens 23 and an image pickup device 24. The position detecting section 25 includes a magnet 26, a sensor 27, and a differential amplifying section 28.

The processor 3 includes a lens driving circuit 30, a driving control section 31, and a position detection circuit 32. The position detection circuit 32 includes an analog digital converter (hereinafter referred to as ADC) 33 and a power supply circuit 34.

The lens driving section 20 advances and retracts the objective lens 23 held by the lens frame 21 in a longitudinal direction of the insertion section 10 on the basis of a current value outputted from the lens driving circuit 30. As the lens driving section 20, for example, a voltage actuator or a motor is used. A focal position can be changed by advancing and retracting the objective lens 23 in the longitudinal direction of the insertion section 10 by the lens driving section 20.

The objective lens 23 forms an optical image of an illuminated object. The image pickup device 24 is an image sensor such as a CCD or a CMOS. A light receiving surface of the image pickup device 24 is disposed in an image forming position of the objective lens 23. The image pickup device 24 generates an image pickup signal by picking up an optical image of the object and outputs the generated image pickup signal to the processor 3 via a signal line (not shown in the figure) incorporated in the endoscope 2.

The processor 3 includes a video signal processing circuit (not shown in the figure) configured to apply predetermined video signal processing to the image pickup signal outputted from the image pickup device 24. The processor 3 applies the predetermined video signal processing to the image pickup signal and generates a predetermined video signal. The processor 3 outputs the generated predetermined video signal to the monitor 4 to cause the monitor 4 to, as explained above, display, as a video, the optical image (the endoscopic image) picked up by the image pickup device.

The magnet 26 is disposed in the lens frame 21. The sensor 27 detects a position of the magnet 26 according to an electric current supplied from the power supply circuit 34 of the position detection circuit 32 of the processor 3 and outputs a result of the detection to the differential amplifying section 28. The differential amplifying section 28 differentially amplifies the detection result outputted from the sensor 27 and outputs the detection result to the ADC 33 of the position detection circuit 32 of the processor 3. The power supply circuit 34 generates electric power for the sensor 27 and the differential amplifying section 28 and outputs the electric power to the sensor 27 and the differential amplifying section 28. The power supply circuit 34 configures a reference-voltage generating section configured to generate a reference voltage supplied to the differential amplifying section 28. The generated reference voltage is supplied to the differential amplifying section 28 of the endoscope 2 via the cable 15. An output signal of the differential amplifying section 28 is detected by the processor 3 via the cable 15.

When the electric power for the sensor 27 is supplied by a constant current circuit of the power supply circuit 34, a voltage in the sensor 27 portion varies according to fluctuation in resistance of the cable 15 and the connector section 16. However, a voltage difference of the sensor 27 portion is determined and stabilized irrespective of the fluctuation in the resistance of the cable 15 and the connector section 16. Consequently, an output signal of the sensor 27 is stably outputted with respect to GND potential of the sensor 27. Therefore, even if the resistance of the cable 15 or the connector section 16 fluctuates, the output signal of the sensor 27 can be highly accurately detected by the differential amplifying section 28.

The ADC 33 converts the signal outputted from the differential amplifying section 28 from an analog signal into a digital signal and outputs the signal to the driving control section 31. The driving control section 31 determines a value of an electric current fed to the lens driving section 20 such that the position of the objective lens 23 is set in a desired position and outputs information concerning the determined current value to the lens driving circuit 30.

The lens driving circuit 30 is a driver circuit configured to feed an electric current to the lens driving section 20. The lens driving circuit 30 outputs to the lens driving section 20 the electric current whose value has been determined by the driving control section 31, according to the information concerning the current value outputted from the driving control section 31.

Figure 3:
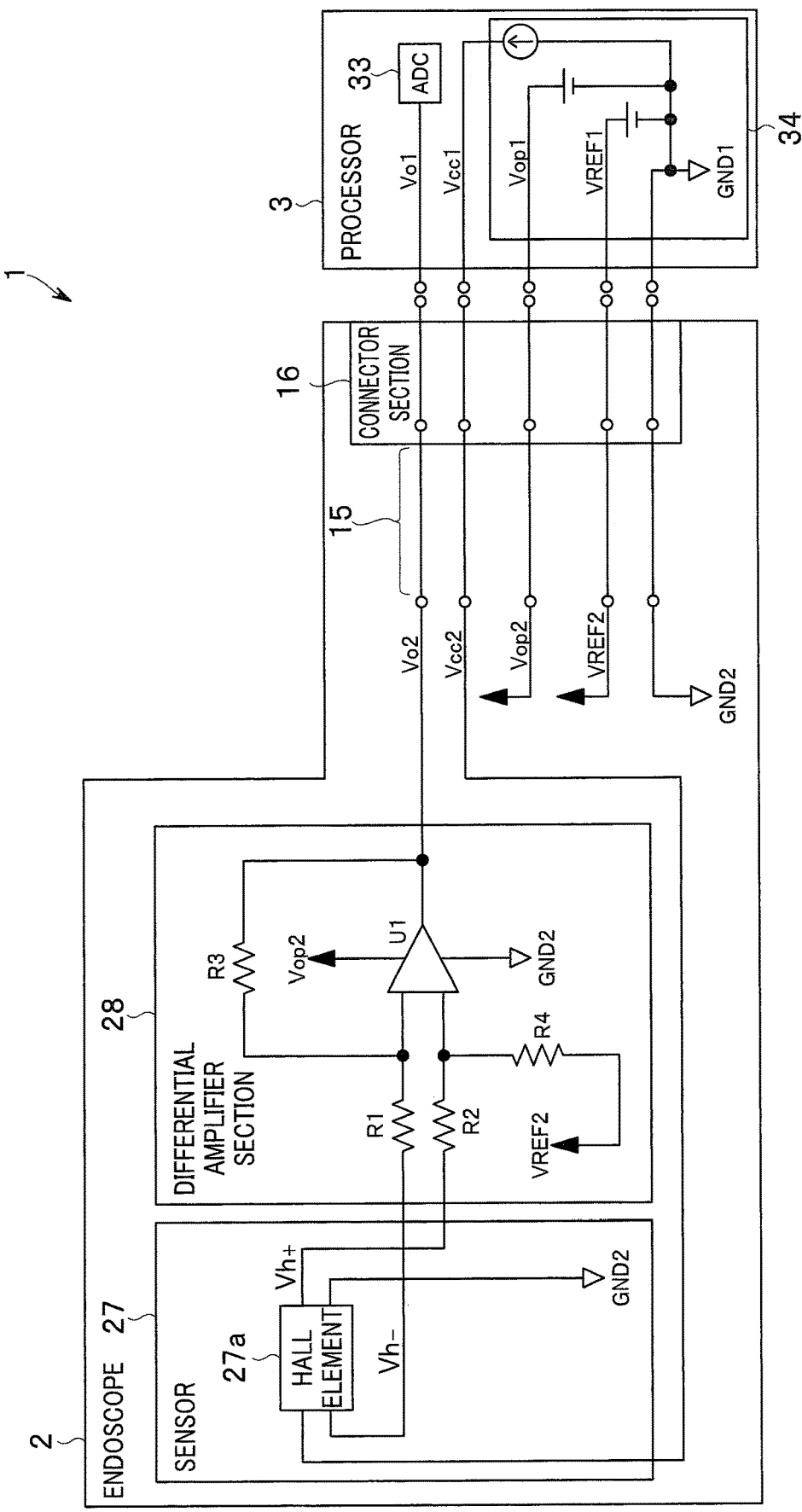
FIG. 3 is a diagram showing detailed configurations of a sensor, a differential amplifying section, and a power supply circuit.

FIG. 3 is a diagram showing detailed configurations of the sensor, the differential amplifying section, and the power supply circuit.

In this embodiment, the sensor 27 configured to detect the position of the magnet 26 is configured by a Hall element 27a configured to detect a magnetic field. The Hall element 27a includes two input terminals and two output terminals.

The differential amplifying section 28 is configured by resistors R1 to R4 and an operational amplifier U1. The operational amplifier U1 includes a non-inverting input terminal, an inverting input terminal, and an output terminal. The constant current circuit 34 generates power supply voltages of GND1, VREF1, Vop1, and Vcc1 and supplies the power supply voltages to the sensor 27 and the differential amplifying section 28 via the connector section 16 and the cable 15.

A power supply Vcc2 from the processor 3 is connected to one input terminal of the Hall element 27a. A ground GND2 from the processor 3 is connected to the other input terminal. One output terminal of the Hall element 27a is connected to the inverting input terminal of the operational amplifier U1 via the resistor R1. The other output terminal of the Hall element 27a is connected to the non-inverting input terminal of the operational amplifier U1 via the resistor R2. A reference voltage VREF2 is connected to the non-inverting input terminal of the operational amplifier U1 via the resistor R4.

The operational amplifier U1 of the differential amplifying section 28 receives the VREF1 in the resistor R4 generally having a high resistance value. Therefore, because an electric current hardly flows in the cable 15, VREF1≈VREF2. That is, the operational amplifier U1 of the differential amplifying section 28 receives a reference voltage with input resistance higher than total resistance of output resistance of the reference voltage, resistance of the cable 15, and resistance of the connector section 16.

As a result, because the differential amplifying section 28 receives the reference voltage with the input resistance higher than the total of the output resistance of the reference voltage, the resistance of the cable, and the resistance of the connector section 16, a voltage drop of the reference voltage can be prevented.

Potential Vo2 outputted from the output terminal of the operational amplifier U1 is inputted to the inverting input terminal via the resistor R3. Potential Vo2 outputted from the operational amplifier U1 is inputted to the ADC 33 of the position detection circuit 32 of the processor via the cable 15 and the connector section 16.

At this time, the potential Vo2 is changed to the potential Vo1 by the cable 15 and inputted to the ADC 33. However, when the potential Vo2 is received by an element having high input impedance such as the ADC 33, an electric current hardly flows to the cable 15. Therefore, Vo2≈Vo1. That is, the ADC 33 of the processor 3 receives the output signal outputted from the differential amplifying section 28 with input resistance higher than total resistance of output resistance of the differential amplifying section 28, resistance of the cable 15, and resistance of the connector section 16.

As a result, because the processor 3 receives the signal amplified by the distal end portion 11 of the endoscope 2 with the input resistance higher than a total of output resistance of the amplified signal, the resistance of the cable 15, and the resistance of the connector section 16, the amplified signal can be highly accurately detected by A/D conversion or the like.

The potential Vo2 outputted from the operational amplifier U1 is represented by Expression (1). Resistance values of the resistors R1 to R4 are generally set to satisfy Expression (2). Therefore, the potential Vo2 outputted from the operational amplifier U1 is finally determined by differential amplification of an output of the sensor 27 and the reference voltage VREF2 as indicated by Expression (3).

Expression 1

$$Vo2 = \frac{R3}{R1}(Vh_+ - Vh_-) + \left(1 - \frac{R2}{R1} \times \frac{R1+R3}{R2+R4}\right)Vh_+ + \frac{R2}{R1} \times \frac{R1+R3}{R2+R4} \times VREF2 \quad (1)$$

Expression 2

$$\frac{R2}{R1} \times \frac{R1+R3}{R2+R4} \approx 1 \quad (2)$$

Expression 3

$$Vo2 \approx \frac{R3}{R1}(Vh_+ - Vh_-) + VREF2 \quad (3)$$

Electric power Vop2 and the ground GND2 are supplied to the operational amplifier U1. Because an electric current flows to the operational amplifier U1, a voltage drop occurs in the cable 15, and Vop1>Vop2. However, this voltage does not affect signal detection accuracy of the sensor 27.

Because an electric current of the sensor 27 and an electric current of the operational amplifier U1 flow to the cable 15 that connects the ground GND1 and the ground GND2, the ground GND1<the ground GND2. However, this voltage substantially does not affect the signal detection accuracy of the sensor 27.

Figure 4:
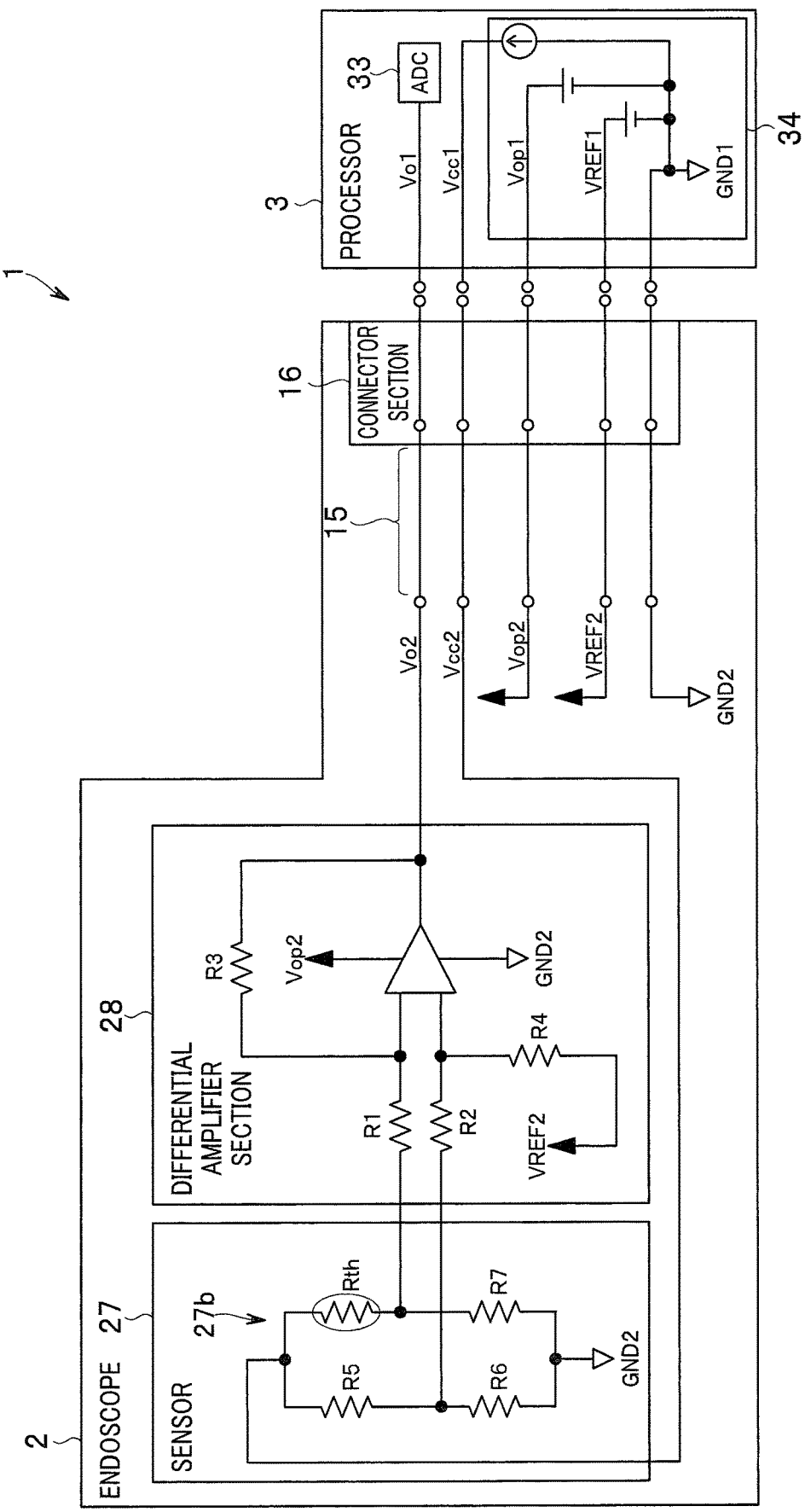
FIG. 4 is a diagram for explaining another configuration of a sensor 27.
Figure 5:
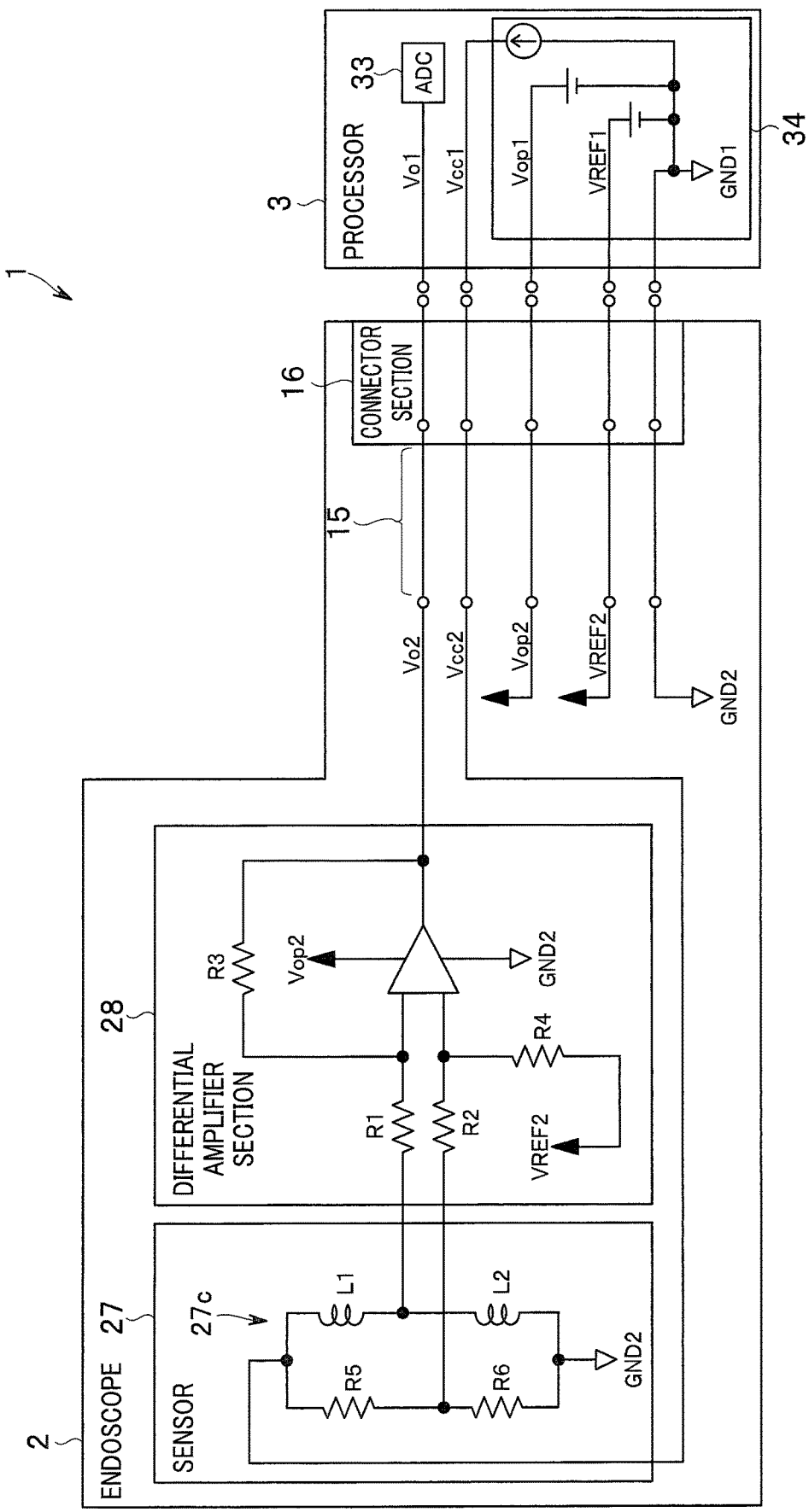
FIG. 5 is a diagram for explaining another configuration of the sensor 27.

Note that, in this embodiment, the sensor 27 is configured as the Hall element 27a to detect the magnetic field of the magnet 26. However, the sensor 27 is not limited to the Hall element 27a. FIG. 4 and FIG. 5 are diagrams for explaining another configuration of the sensor 27.

As shown in FIG. 4, the sensor 27 is configured by a bridge circuit 27b. The bridge circuit 27b includes a thermosensitive element Rth and resistors R5, R6, and R7. The thermosensitive element Rth is, for example, an NTC (negative temperature coefficient) thermistor of a chip type having a negative temperature characteristic. When temperature rises, a resistance value of the thermosensitive element Rth decreases. Because the sensor 27 includes the thermosensitive element Rth, it is possible to detect temperature. Note that the thermosensitive element Rth is not limited to the NTC thermistor. A PTC (positive temperature coefficient) thermistor or a CTR (critical temperature resistor) thermistor may be used.

As shown in FIG. 5, the sensor 27 is configured by a bridge circuit 27c. The bridge circuit 27c includes coils L1 and L2 and the resistors R5 and R6. Because the bridge circuit 27c includes the coils L1 and L2, it is possible to detect a change in inductance. Note that the bridge circuit 27c includes the two coils L1 and L2. However, the bridge circuit 27c may include at least one coil L1.

As explained above, in the endoscope apparatus 1, the sensor 27 and the differential amplifying section 28 are disposed in the endoscope 2. The reference voltage of the differential amplifying section 28 is supplied from the processor 3. The differential amplifying section 28 receives the supplied reference voltage with high input impedance.

Conventionally, in the endoscope 2, the long cable 15 and the connector section 16 of a detachable type are used. The resistance of the long cable 15 and the connector section 16 varies according to an environment of use (temperature dependency) and the like. Therefore, fluctuation in GND potential of the endoscope 2 is large. An output signal of the sensor 27 based on the fluctuating GND potential also varies.

On the other hand, in this embodiment, the endoscope apparatus 1 differentially amplifies an output signal of the sensor 27 and generates a reference voltage (an offset voltage) with the processor 3 having stable GND potential and supplies the reference voltage to the differential amplifying section 28 to thereby reduce the variation of the output signal and highly accurately detect the output signal of the sensor 27.

That is, in the endoscope 2, the cable 15 is long and electric resistance of the cable 15 has temperature dependency. The resistance of the cable 15 fluctuates according to this temperature dependency and an electric current flows to a GND line of the endoscope 2, whereby GND potential in the endoscope 2 fluctuates. Therefore, when an output signal of the sensor 27 is detected on the basis of the GND potential, the output signal is affected by the fluctuation in the GND potential and cannot be highly accurately amplified and detected.

To solve this problem, in the endoscope apparatus 1 of this embodiment, the differential amplifying section 28 is mounted on the distal end portion 11. The reference voltage VREF2 (VRE1≈VREF2) to the differential amplifying section 28 is generated by the processor 3 having stable GND potential and supplied to the differential amplifying section 28. Consequently, the differential amplifying section 28 can highly accurately amplify an output signal of the sensor 27 irrespective of GND potential at the distal end portion 11 of the endoscope 2 on the basis of the inputted reference voltage VREF2. As a result, the processor 3 is capable of highly accurately detecting the output signal of the sensor 27.

Accordingly, the processor can highly accurately measure an output signal of the sensor mounted on the endoscope with the endoscope apparatus of this embodiment even when GND potential at the distal end portion of the endoscope fluctuates according to temperature dependency of cable resistance.

Dirt such as water scale is stuck to the connector section 16 of the endoscope 2 in an environment of actual use. A contact resistance value of the connector section 16 fluctuates. Contact resistance of the connector section 16 is also a factor that causes fluctuation in GND potential. However, an output signal of the sensor 27 can be highly accurately detected with the configuration of this embodiment even if the contact resistance of the connector section 16 fluctuates.

When the sensor 27 is mounted on the distal end portion 11 of the endoscope 2 as in this embodiment, because the cable 15 is long, fluctuation in resistance of the cable 15 is large. Further, when the endoscope 2 enters a body of a patient having higher temperature than an ambient temperature, a temperature distribution occurs in the cable 15. Fluctuation in resistance due to temperature dependency of the cable 15 increases. Even when the cable 15 is long and the temperature dependency of the cable 15 increases, the output signal of the sensor 27 can be highly accurately detected with the configuration of this embodiment.

Second Embodiment

A second embodiment is explained.

Figure 6:
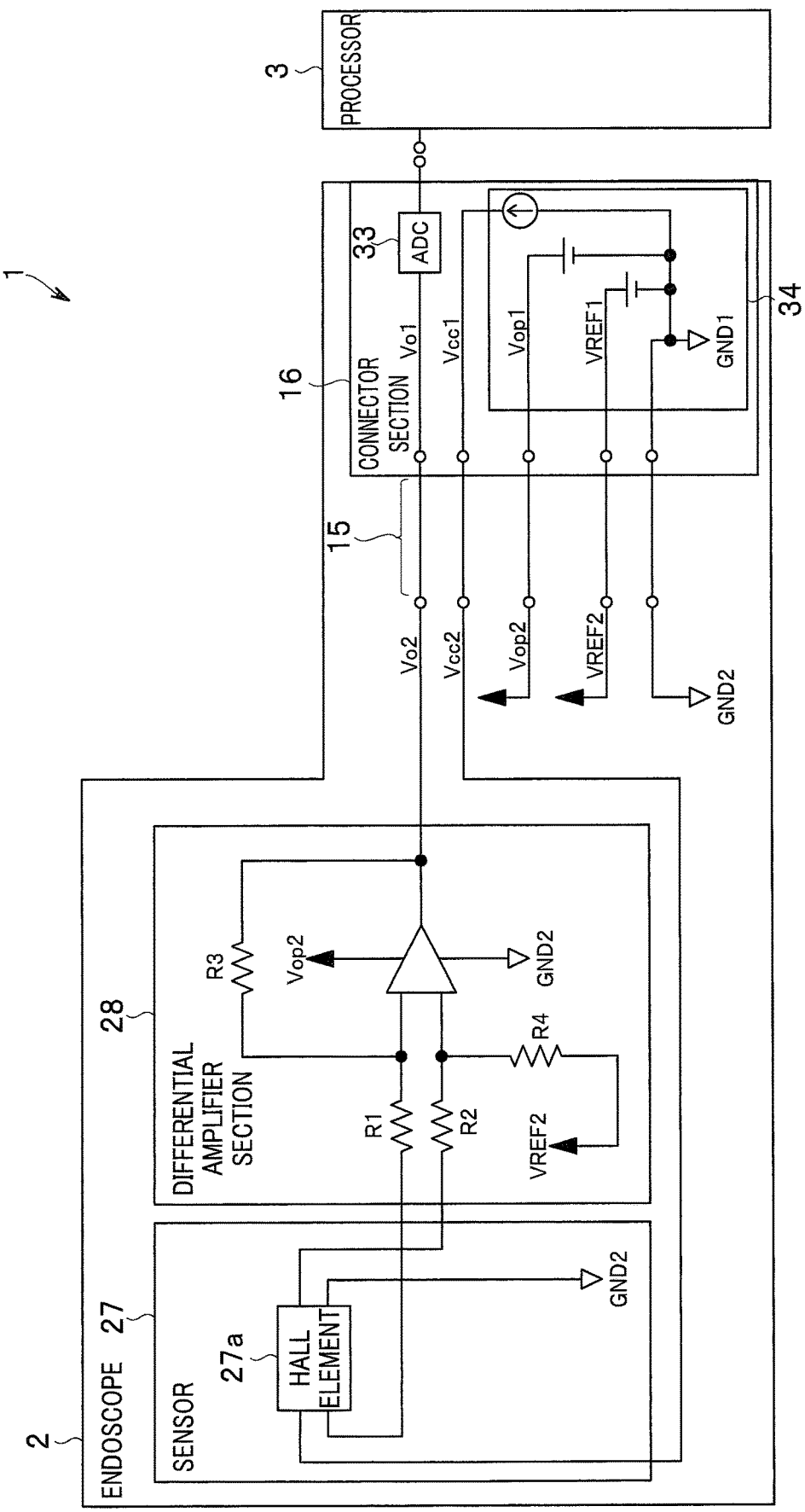
FIG. 6 is a configuration diagram for explaining a detailed configuration of an endoscope according to a second embodiment.

FIG. 6 is a configuration diagram for explaining a detailed configuration of an endoscope according to the second embodiment. Note that, in FIG. 6, the same components as the components shown in FIG. 2 are denoted by the same reference numerals and signs and explanation of the components is omitted.

The endoscope 2 of the second embodiment includes a connector section 16a instead of the connector section 16 shown in FIG. 2. In the connector section 16a, the ADC 33 and the power supply circuit 34 provided in the processor 3 in the first embodiment are provided. The other components are the same as the components in the first embodiment.

In the endoscope 2 of this embodiment, the generation of the reference voltage by the power supply circuit 34 and the analog-digital conversion of the output signal of the sensor 27 by the ADC 33 are performed by the connector section 16a. As a result, the endoscope 2 of this embodiment can perform detection of the output signal of the sensor 27 with reduced fluctuation in GND potential of the sensor 27 and the differential amplifying section 28 due to the temperature dependency of the resistance of the cable 15.

The present invention is not limited to the embodiments and the modifications explained above. Various changes, alterations, and the like are possible in a range in which the gist of the present invention is not changed.

What is claimed is:

1. An endoscope apparatus comprising:
   a processor;
   an endoscope comprising:
      a sensor configured to generate a first output signal; and
      a differential amplifier circuit;
   a cable configured to be connected to the endoscope; and
   a connector configured to detachably connect the cable to the processor,
   wherein the processor comprises a reference-voltage generating circuit configured to generate a reference voltage and output the reference voltage to the differential amplifier circuit via the connector and the cable,
   wherein the differential amplifier circuit is configured to differentially amplify the first output signal generated by the sensor to generate a second output signal, and to output the second output signal to the processor via the cable and the connector, and
   wherein the differential amplifier circuit is configured to receive the reference voltage with input resistance higher than total resistance of output resistance of the reference voltage, resistance of the cable, and resistance of the connector.

2. The endoscope apparatus according to claim 1, wherein the sensor is disposed at a distal end portion of the endoscope.

3. The endoscope apparatus according to claim 1, wherein the differential amplifier circuit comprises an operational amplifier.

4. The endoscope apparatus according to claim 3, wherein the processor is configured to receive the second output signal with input resistance higher than total resistance of output resistance of the operational amplifier, the resistance of the cable, and the resistance of the connector.

5. The endoscope apparatus according to claim 1, wherein the processor comprises a constant current circuit configured to supply a power supply voltage to the sensor.

6. The endoscope apparatus according to claim 1, wherein the sensor comprises a Hall element.

7. The endoscope apparatus according to claim 1, wherein the sensor comprises a bridge circuit, and wherein the bridge circuit comprises a thermosensitive element configured to detect temperature.

8. The endoscope apparatus according to claim 1, wherein the sensor comprises a bridge circuit, wherein the bridge circuit comprises one or two coils, wherein a power supply voltage supplied to the sensor includes an AC voltage, and wherein the bridge circuit is configured to detect a change in inductance of the one or two coils.

9. An endoscope comprising:
   a cable;
   a sensor configured to generate a first output signal;

a connector; and a differential amplifier circuit configured to differentially amplify the first output signal generated by the sensor to generate a second output signal, and to output the second output signal to the connector via the cable, wherein the connector comprises a reference-voltage generating circuit configured to generate a reference voltage and to output the reference voltage to the differential amplifier circuit via the connector and the cable, and wherein the differential amplifier circuit is configured to receive the reference voltage with input resistance higher than total resistance of output resistance of the reference voltage, resistance of the cable, and resistance of the connector.

10. The endoscope according to claim 9,
wherein the sensor is disposed at a distal end portion of the endoscope.

11. The endoscope according to claim 9,
wherein the differential amplifier circuit comprises an operational amplifier.

12. The endoscope according to claim 11,
wherein the connector is configured to receive the second output signal with input resistance higher than total resistance of output resistance of the operational amplifier, the resistance of the cable, and the resistance of the connector.

13. The endoscope according to claim 9,
wherein the connector comprises a constant current circuit configured to supply a power supply voltage to the sensor.

* * * * *